(12) United States Patent
Kloke et al.

(10) Patent No.: US 8,663,673 B2
(45) Date of Patent: Mar. 4, 2014

(54) DEVICES, ARTICLES, COATINGS, AND METHODS FOR CONTROLLED ACTIVE AGENT RELEASE OR HEMOCOMPATIBILITY

(75) Inventors: Timothy M. Kloke, Chaska, MN (US); Robert W. Hergenrother, Eden Prairie, MN (US); Laurie R. Lawin, New Brighton, MN (US)

(73) Assignee: Surmodics, Inc., Eden Prairie, MN (US)

( * ) Notice: Subject to any disclaimer, the term of this patent is extended or adjusted under 35 U.S.C. 154(b) by 1764 days.

(21) Appl. No.: 11/493,346

(22) Filed: Jul. 26, 2006

(65) Prior Publication Data

US 2007/0026037 A1 Feb. 1, 2007

Related U.S. Application Data

(60) Provisional application No. 60/703,555, filed on Jul. 29, 2005, provisional application No. 60/733,423, filed on Nov. 3, 2005.

(51) Int. Cl.
*A61F 13/00* (2006.01)

(52) U.S. Cl.
USPC ........... 424/422; 424/423; 623/1.1; 623/1.42; 623/2.1; 623/3.1; 623/4.1; 623/9; 623/10; 623/11.11; 623/16.11

(58) Field of Classification Search
USPC ...................................................... 424/70.31
See application file for complete search history.

(56) References Cited

U.S. PATENT DOCUMENTS

| | | | |
|---|---|---|---|
| 4,638,045 A | 1/1987 | Kohn et al. | |
| 5,344,455 A | 9/1994 | Keogh et al. | |
| 5,354,264 A * | 10/1994 | Bae et al. | 604/21 |
| 5,466,233 A | 11/1995 | Weiner et al. | |
| 5,563,056 A | 10/1996 | Swan et al. | |
| 5,788,687 A | 8/1998 | Batich et al. | |
| 5,840,387 A | 11/1998 | Berlowitz-Tarrant et al. | |
| 6,110,483 A | 8/2000 | Whitbourne et al. | |
| 6,214,901 B1 | 4/2001 | Chudzik et al. | |
| 6,306,419 B1 | 10/2001 | Vachon et al. | |
| 6,719,750 B2 | 4/2004 | Varner et al. | |
| 7,056,533 B2 | 6/2006 | Chudzik et al. | |
| 2002/0188037 A1 | 12/2002 | Chudzik et al. | |
| 2003/0014036 A1 | 1/2003 | Varner et al. | |
| 2003/0129130 A1 | 7/2003 | Guire et al. | |
| 2004/0133155 A1 | 7/2004 | Varner et al. | |
| 2004/0142910 A1 | 7/2004 | Vachon et al. | |
| 2005/0019371 A1 | 1/2005 | Anderson et al. | |
| 2005/0059956 A1 | 3/2005 | Varner et al. | |
| 2005/0143363 A1 | 6/2005 | De Juan et al. | |
| 2005/0271703 A1 | 12/2005 | Anderson et al. | |
| 2005/0271706 A1 | 12/2005 | Anderson et al. | |
| 2005/0276837 A1 | 12/2005 | Anderson et al. | |
| 2005/0281863 A1 | 12/2005 | Anderson et al. | |
| 2005/0287188 A1 | 12/2005 | Anderson et al. | |
| 2006/0013854 A1 * | 1/2006 | Strickler et al. | 424/423 |
| 2006/0110428 A1 | 5/2006 | deJuan et al. | |

FOREIGN PATENT DOCUMENTS

| | | |
|---|---|---|
| EP | 0 942 003 A1 | 9/1999 |
| EP | 1 026 219 A1 | 8/2000 |
| WO | WO 00/40628 | 7/2000 |
| WO | WO 01/83866 A2 | 11/2001 |
| WO | WO 2006/116348 A2 | 11/2006 |
| WO | WO 2006/121669 A2 | 11/2006 |

OTHER PUBLICATIONS

Anderson, A. et al., "Platelet Deposition and Fibrinogen Binding on Surfaces Coated with Heparin or Friction-Reducing Polymers," *AJNR*, vol. 17, pp. 859-863 (May 1996).

Kojima, H. et al., "Controlled Drug Diffusion for Oral Extended Release of Highly Water-soluble Drugs Utilizing their Micelle-forming Property and Counter Polymer," *31st Annual Meeting and Exposition of the Controlled Release Society*, Honolulu, Hawaii, Podium Sessions, 5 pages (Jun. 12-16, 2004).

Konar, N. et al., "Drug release from drug-polyanion complex tablets: poly(acrylamido-2-methyl-l-propanesulfonate sodium-co-methyl methacrylate)," *Journal of Controlled Release*, vol. 57, pp. 141-150 (1999).

Kwon, I. et al., "Drug release from electric current sensitive polymers," *Journal of Controlled Release*, vol. 17, pp. 149-156 (1991).

Wabers, H. et al., "Biostability and blood-contacting properties of sulfonate grafted polyurethane and Biomer," *J. Biomater. Sci. Polymer Edn.*, vol. 4, No. 2, pp. 107-133 (1992).

International Search Report mailed May 2, 2007.

Bae et al., Pulsatile Drug Release by Electric Stimulus, *American Chemical Society Symposium Series*, 545, pp. 98-110, 1994.

Kwon et al., "Stimuli Sensitive Polymers for Drug Delivery Systems," *Makromol. Chem. Macromol. Symp.*, 33, 265-277 (1990).

* cited by examiner

*Primary Examiner* — James Rogers
(74) *Attorney, Agent, or Firm* — Kagan Binder, PLLC

(57) ABSTRACT

The present invention relates to devices, articles, coatings, and methods for controlled active agent release and/or for providing a hemocompatible surface. More specifically, the present invention relates to copolymer compositions and devices, articles, and methods regarding the same for controlled active agent release. In an embodiment, the present invention includes a copolymer composition. The copolymer composition can include a copolymer and an active agent. In an embodiment, the copolymer includes an effective portion of a monomeric unit including a polar moiety. The active agent can be polar. The active agent can be charged. The active agent can be non-polar. In an embodiment, the copolymer composition includes a random copolymer. In an embodiment, the random copolymer includes butyl methacrylate-co-acrylamido-methyl-propane sulfonate copolymer, which can provide reduced platelet adhesion.

23 Claims, 7 Drawing Sheets

PBMA coating

PBMA-co-(30%)AMPS sodium salt

PBMA-co-(30%)AMPS acidic form

DEVICES, ARTICLES, COATINGS, AND METHODS FOR CONTROLLED ACTIVE AGENT RELEASE OR HEMOCOMPATIBILITY

CROSS REFERENCE TO RELATED APPLICATIONS

This application claims benefit of Provisional Application No. 60/703,555, filed Jul. 29, 2005 and Provisional Application No. 60/733,423, filed Nov. 3, 2005, which applications are incorporated herein by reference.

FIELD OF THE INVENTION

The present invention relates to compositions including and methods employing a copolymer composition including an effective amount of monomeric unit or monomeric units including polar moieties and at least one second monomeric unit without a charged moiety. The present invention relates to copolymer compositions and devices, articles, and methods for controlled active agent release or for hemocompatibility. The polymer composition can include an active agent. Such a composition can provide controlled active agent release. The polymer composition can provide a hemocompatible surface, for example, for an implantable device.

BACKGROUND OF THE INVENTION

Therapeutic benefits can be achieved in some instances by providing an active agent to a subject in a manner that extends the time over which the active agent is released. Further, therapeutic benefits can be achieved by providing an active agent to a specific target tissue, instead of systemically. This is because the effect of the agent on the target tissue can be maximized while limiting side effects on other tissues. One approach to providing these benefits is to use a drug polymer delivery system containing an active agent on a medical device. The coating can serve to control the rate at which an active agent is eluted while the fact that it is on a medical device allows the delivery to be in proximity to specific tissues.

Controlling the drug release rate for drug delivery systems is desirable for achieving an effective therapeutic level. Some active agents elute through current drug polymer delivery systems too quickly, others do not elute fast enough. This is partly because active agents are very diverse in their chemical properties including size, hydrophobicity, charge, etc. and these properties affect their interaction with the drug polymer delivery system components and elution medium. For example, small hydrophilic agents such as trigonelline-HCL, diclofenac and chlorhexidine diacetate typically elute with large initial bursts from current drug polymer delivery systems and, therefore, demonstrate poor elution rate control. Bioactive agents can have divergent properties and it can be a challenge to obtain a polymer delivery system that can control both the release of hydrophilic and hydrophobic active agents. A drug delivery polymer system may elute both hydrophilic and hydrophobic drugs at a defined rate, but, often the polymer system is limited by its ability to achieve variations in the release rate.

Therefore, a need exists for a drug polymer delivery system that can provide an effective elution profile with one or more of a variety of active agents.

Two general strategies that have been used to develop improved blood-contacting materials include modifying the chemistry of the bulk material itself, and/or modifying the interfacial properties of the material. With regard to the latter approach, several classes of materials have been covalently bonded onto blood-contacting surfaces with the goal of improving blood compatibility. These include anticoagulants, such as heparin and hirudin; hydrogels; polyethylene oxide (PEO); albumin binding agents; cell membrane components; prostaglandins; and certain polymers. These approaches have met with varying degrees of success in terms of reducing protein adsorption, platelet adhesion and activation, and thrombus formation.

Therefore, a need exists for a coating or material that can provide effective hemocompatibility.

SUMMARY OF THE INVENTION

The present invention relates to compositions including and methods employing a copolymer composition including an effective amount of monomeric unit or monomeric units including polar moieties and at least one second monomeric unit without a charged moiety. The polymer composition can include an active agent. Such a composition can provide controlled active agent release. The polymer composition can provide a hemocompatible surface, for example, for an implantable device.

The present invention relates to devices, articles, coatings, and methods for providing controlled active agent release. Embodiments of the present invention include devices, articles, coatings, and methods including a copolymer composition including an active agent.

In an embodiment, the present invention includes a copolymer composition. The copolymer composition can include a copolymer and an active agent. In an embodiment, the copolymer includes an effective portion of a monomeric unit including a polar moiety. The active agent can be polar. The active agent can be charged. The active agent can be nonpolar. In an embodiment, the copolymer composition includes a random copolymer. In an embodiment, the random copolymer includes butyl methacrylate-co-acrylamido-methyl-propane sulfonate copolymer.

The present invention relates to devices, articles, coatings, and methods for providing hemocompatibility. Embodiments of the present invention include devices, articles, coatings, and methods including a copolymer composition effective for providing hemocompatibility.

In an embodiment, the present invention includes a hemocompatible copolymer composition. In an embodiment, the hemocompatible copolymer includes an effective proportion of a monomeric unit including a polar moiety. In an embodiment, the copolymer composition includes a random copolymer. In an embodiment, the hemocompatible random copolymer includes butyl methacrylate-co-acrylamido-methyl-propane sulfonate copolymer.

In an embodiment, the present invention includes an article including the copolymer composition. The article can be a medical device. The medical device can include a structure configured for introduction into a subject and the copolymer composition disposed on the structure. The article can be a substrate. The substrate can include the copolymer composition disposed on a surface. The article can be formed from the copolymer composition or can include a core of the copolymer composition.

DETAILED DESCRIPTION OF THE INVENTION

Definitions

Figure 1:
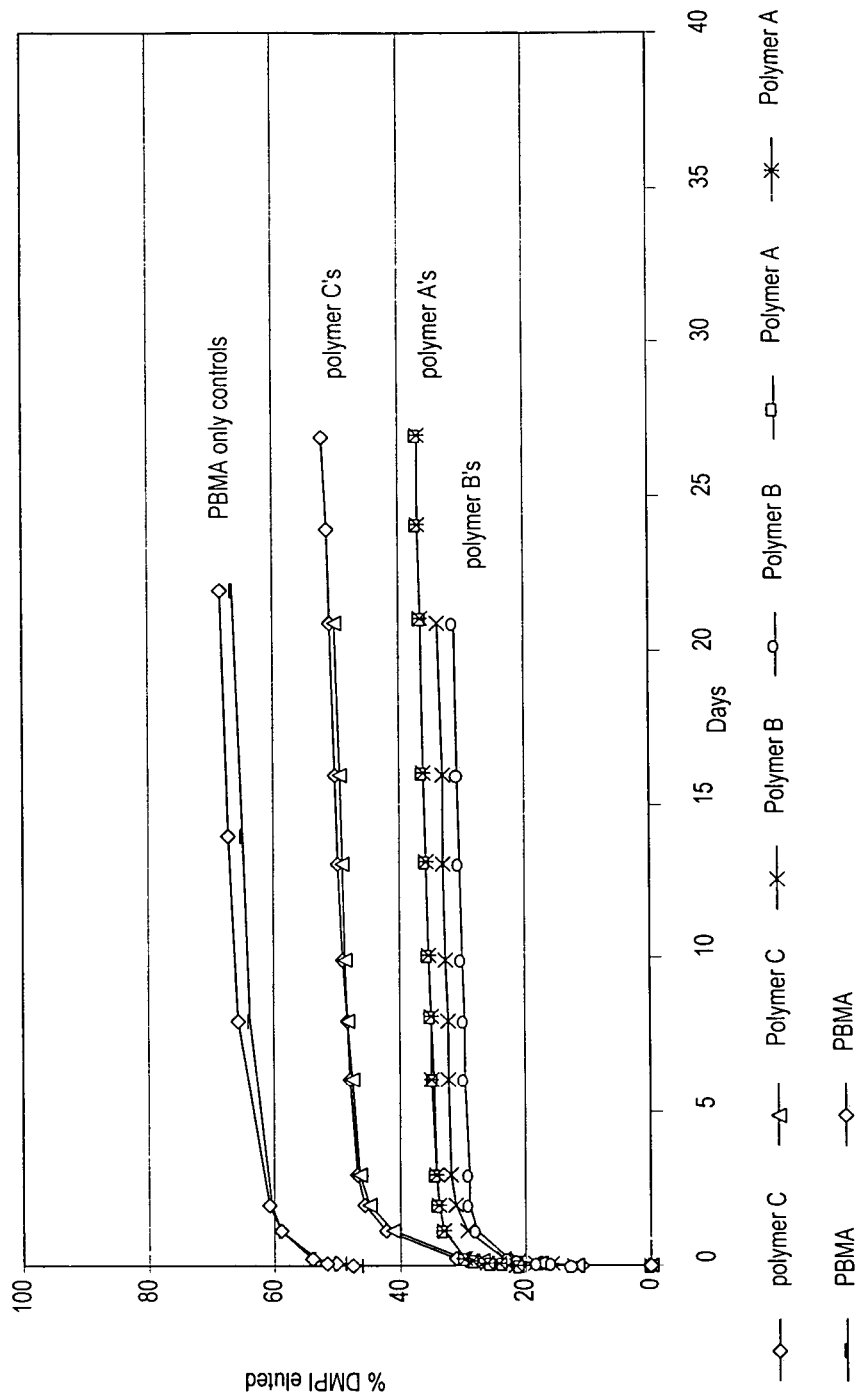
FIG. 1 schematically illustrates the amount of active agent DMPI eluted over time from control coatings and copolymer coatings according to the present invention.

As used herein, the term "polar" refers to a molecule or moiety exhibiting polarity, for example, having a dipole. A polar molecule or moiety can have, for example, a partial or full positive charge in one region and a partial or full negative charge in a second region. Polar molecules or moieties include hydrophilic molecules or moieties. Polar moieties include hydroxyl, amide, ether, thiol, thioether, ester, thioester, borane, borate, and metal complexes, amine, carbonyl, and the like. Polar moieties also include charged moieties. A polar molecule or moiety can have, for example, a positive charge, a negative charge, or both a positive charge and a negative charge (e.g., as an inner salt).

As used herein, the term "charge" or "charged" refers to a molecule or moiety having a positive charge, a negative charge, or both a positive charge and a negative charge (e.g., as an inner salt) and salts of such molecules or moieties. Suitable positively charged molecules or moieties (e.g., at neutral pH in aqueous compositions) include amines, quaternary ammonium moieties, sulfonium, phosphonium, ferrocene, or the like. Suitable negatively charged molecules or moieties (e.g., at neutral pH in aqueous compositions) include carboxylates, alkoxylates, phenols substituted with strongly electron withdrawing (attracting) groups (e.g., tetrachlorophenols), phosphates, phosphonates, phosphinates, sulphates, sulphonates; thiocarboxylates, hydroxamic acids, nitro, or the like.

As used herein, the terms "treat", "treating", "treatment", and "therapy" refer to reducing, alleviating, slowing the progression of, ameliorating, attenuating, prophylaxis, or otherwise lessening one or more symptoms, causes, or effects of a disease or disorder. The term "prevent", as used herein, refers to putting off, delaying, slowing, inhibiting, or otherwise stopping, reducing or ameliorating the onset of a disease or disorder.

As used herein, the term "preformed polymer" means a polymer which has already been polymerized before application, as opposed to a monomer or macromere which has not yet been polymerized and can be polymerized as it is applied or after it is applied.

As used herein, the term "about" modifying the quantity of an ingredient in the compositions of the invention or employed in the methods of the invention refers to variation in the numerical quantity that can occur, for example, through typical measuring and reagent handling procedures used for making polymer compositions, coated substrates, and medical devices in the real world; through inadvertent error in these procedures; through differences in the manufacture, source, or purity of the ingredients employed to make the compositions or carry out the methods; and the like. Whether or not modified by the term "about", the claims include equivalents to the quantities.

Copolymer Compositions

The present invention relates to compositions including and methods employing a copolymer composition including an effective amount of monomeric unit or monomeric units including polar moieties and at least one second monomeric unit without a charged moiety. The polymer composition can include an active agent. Such a composition can provide advantageous elution of polar or hydrophobic active agents. The polymer composition can provide a hemocompatible surface, for example, for an implantable device.

Specific embodiments of the copolymer include random copolymers of butyl methacrylate-co-acrylamido-methylpropane sulfonate (pbma-co-AMPS). In certain embodiments, the random copolymer can include AMPS at about 0.5 to about 30 mol-%, about 1 to about 20 mol-%, or about 2 to about 10 mol-%. In certain embodiments, the random copolymer can include AMPS at about 0.5 to about 30 mol-%, about 10 to about 20, or about 15 mol-%.

The Copolymer Composition

An embodiment of a polymer including an effective amount of monomeric unit or monomeric units including polar moieties and at least one second monomeric unit (without charged moiety) can be represented, for example, by Formula A:

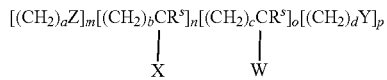

In Formula A: Each [ ] moiety represents a monomeric unit present in the polymer, which can be present in any order, e.g., randomly. Each $R^s$ is independently H or $CH_3$. Each of a, b, c, and d is independently 1-4, 1-3, 1-2, 1, 2, or 3.

Each X and Z is independently a polar moiety. For example, in an embodiment, X can be or include a methyl propane sulfonate moiety (e.g., amido isobutyl sulfonate (—C(O)NHC(CH$_3$)$_2$CH$_2$SO$_3$H, the pendant moiety in the monomer AMPS)). For example, in an embodiment, X can be or include a methyl propane sulfonate moiety and Z is absent (m=0). In certain embodiments, X can be or include a carboxyl containing moiety, a quaternary ammonium containing moiety, a pyridinium containing moiety, combinations thereof, or the like.

Each W and Y is independently a group that is not a charged moiety. W or Y can be or include, for example, a polar or non-polar moiety. W or Y can be or include, for example, alkyl, aryl, methylene, amide, methyl, alcohol, ether, amide, ester, carbamate, carbonate, combinations thereof, or the like. In an embodiment, W can be or include a —C(O)O—(CH$_2$)$_3$CH$_3$ moiety (the pendant moiety of the monomer butyl methacrylate).

In Formula A, each of m, n, o, and p represents the mole fraction of the corresponding monomeric unit in the polymer, and m+n represents an effective mole fraction. For example, m+n can be about 0.5 to about 30 mol-%, about 1 to about 20 mol-%, or about 2 to about 10 mol-%. By way of further example, m+n can be about 1.5 mol-%, about 3 mol-%, or about 9 mol-%. Either m or n can be zero, but m+n>0. The present polymer can include any of these ranges or amounts not modified by about or any of these quantities individually.

Either o or p can be zero, but o+p>0.

Suitable random copolymers can include polar monomeric units such as water soluble monomeric units. Water soluble monomeric units include those listed as water soluble in the Polymer Handbook (Branderup and Immergut, eds.), 3d Edition (1989) or later, John Wiley and Sons, NY. Suitable random copolymers are soluble in organic solvent.

Suitable random copolymers can include water soluble polar monomeric units such as a water soluble N-substituted acrylamide including a polar or charged substituent (e.g., a cationic or anionic substituent), a water soluble acrylic acid ester including a polar or charged substituent (e.g., a cationic or anionic substituent), a water soluble carboxyl containing monomeric unit, a water soluble quaternary ammonium containing monomeric unit, combinations thereof, or the like. Suitable random copolymers can include an N-substituted acrylamide including a polar substituent such as acrylamido-methyl propane sulfonate (AMPS). Suitable random copolymers can include an N-substituted acrylamide including a charged substituent such as an alkali metal (e.g., sodium) salt of acrylamido-methyl propane sulfonate (AMPS). Suitable random copolymers can include an acrylic acid ester including a polar substituent such as 3-sulfopropyl(meth)acrylate. Suitable random copolymers can include an acrylic acid ester including a charged substituent such as an alkali metal (e.g., sodium) salt of 3-sulfopropyl(meth)acrylate. Suitable random copolymers can include a water soluble N-substituted acrylamide including a cationic substituent such as a water soluble quaternary ammonium substituted acrylamide or methacrylamide.

Suitable random copolymers can include as the second monomeric unit an acrylate or methacrylate. Suitable second monomeric units include N,N-dimethylacrylamide, N,N-diethylacrylamide, N-isopropylacrylamide, N-t-butylacrylamide, N-octylacrylamide, N-cyclohexylacrylamide, N-phenylacrylamide, N-benzylacrylamide, N-methylmethacrylamide, N-ethylmethacrylamide, N,N-dimethylmethacrylamide, N,N-diethylmethacrylamide, alkyl or aryl acrylate, alkyl or aryl methacrylate, vinylmethylether, combinations thereof, or the like. Suitable second monomeric units include a methacrylate, for example, butyl methacrylate.

Suitable polymer backbones including uncharged polar moieties include polyethers (e.g., polyethylene glycol, polypropylene glycol), substituted polyalkyleneimines (e.g., substituted polyethyleneimine), and the like.

Suitable random copolymers include butyl methacrylate-co-acrylamido-methyl-propane sulfonate (pbma-co-AMPS).

The copolymer can include polar monomeric unit at about 0.5 to about 30 mol-%, about 1 to about 20 mol-%, or about 2 to about 10 mol-%. The copolymer can include polar monomeric unit at about 1.5 mol-%, about 3 mol-%, or about 9 mol-%. The copolymer can include second monomeric unit at about 70 to about 99.5 mol-%, about 80 to about 99 mol-%, or about 90 to about 98 mol-%, or about 85 to about 95 mol-%. The copolymer can include second monomeric unit at about 98.5 mol-%, about 97 mol-%, or about 91 mol-%. The present polymer can include any of these ranges or amounts not modified by about or any of these quantities individually.

In an embodiment, the copolymer can include polar monomeric unit at an amount such that the copolymer, when wetted, does not form a hydrogel. In an embodiment, the copolymer can include polar monomeric unit at an amount such that the copolymer, when wetted, does not expand. In an embodiment, the copolymer can include polar monomeric unit at an amount such that the copolymer, when wetted, does not expand significantly.

The present copolymer composition can be applied to a substrate or device using known methods. For example, the copolymer can be mixed with active agent and solvent and applied to a substrate or device by spraying (e.g., aerosol or ultrasonic), dipping, or with an ultrasonic coater. In some embodiments, the present composition can include a preformed polymer. For example, an active agent may be mixed with a preformed polymer and then deposited on a substrate. The method can include drying the device after applying the copolymer composition.

The copolymer composition can be applied at relative humidity of, for example, about 5% to about 75%, about 5% to about 50%, about 5% to about 35%, or about 5% to about 10%. Although not limiting to the present invention, it is believed that applying the present copolymer composition at a higher relative humidity will increase the rate of active agent release compared to a lower humidity.

Compositions Including Copolymer and Active Agent

The present invention includes compositions including copolymer and active agent. In an embodiment, a composition according to the present invention can provide controlled elution of an active agent from the composition. In certain embodiments, the present composition can be employed in a device, an article, a coating, or a method and can, for example, provide controlled elution of the active agent. The copolymer can include at least one polar monomeric unit. The active agent can include at least one polar moiety. In certain embodiments, the copolymer includes at least one polar monomeric unit, the active agent includes a charge, or the copolymer includes at least one polar monomeric unit and the active agent includes a charge. The active agent can be hydrophobic.

In an embodiment, the copolymer includes at least one polar monomeric unit and a second monomeric unit. The copolymer can include an effective amount of monomeric unit or monomeric units including a polar moiety. The amount can be effective, for example, to provide an effective or controlled elution profile for an active agent, such as a polar or charged active agent. The amount can be effective, for example, to provide an effective or controlled elution profile for an active agent, such as a hydrophobic active agent. The polar moiety can be in the polymer backbone or a group pendant from the polymer backbone. The second monomeric unit can be polar or non-polar. For example, the second monomeric unit can be hydrophobic in character. In an embodiment, the copolymer is a random copolymer. A random copolymer can include, for example, at least one polar monomeric unit and a second monomeric unit. A random copolymer is not a block copolymer.

Specific embodiments of the copolymer include random copolymers of butyl methacrylate-co-acrylamido-methyl-propane sulfonate (pbma-co-AMPS). In certain embodiments, the random copolymer can include AMPS at about 0.5 to about 30 mol-%, about 1 to about 20 mol-%, or about 2 to about 10 mol-%. In certain embodiments, the copolymer can include polar monomeric unit at about 1.5 mol-%, about 3 mol-%, or about 9 mol-%. The copolymer can include second monomeric unit at about 70 to about 99.5 mol-%, about 80 to about 99 mol-%, or about 90 to about 98 mol-%, or about 85 to about 95 mol-%. The copolymer can include second monomeric unit at about 98.5 mol-%, about 97 mol-%, or about 91 mol-%. The present polymer can include any of these ranges or amounts not modified by about or any of these quantities individually.

The present coated copolymer composition can include active agent at a concentration of about 2 to about 70 wt-%, about 2 to about 50 wt-%, about 5 to about 50 wt-%, about 5 to about 40 wt-%, about 10 to about 30 wt-%, or about 15 to about 30 wt-%. The present copolymer composition can include active agent at a concentration of about 15 wt-% or about 30 wt-%.

The present composition can provide any of a variety of effective elution profiles for the active agent. In an embodiment, the present composition can provide prolonged release of an active agent. The term "extended release", as used herein, refers to an elution profile exhibiting prolonged release of an active agent compared with an analogous or the same coating lacking the present copolymer composition. Embodiments of the invention include those having extended release profiles. The term "reduced burst", as used herein, refers to an elution profile exhibiting an initial release burst significantly smaller compared with an analogous or the same coating lacking the present copolymer composition. Embodiments of the invention include those having reduced burst release profiles. In an embodiment, the present copolymer composition can provide a linear release profile.

In an embodiment, the present composition can provide a release profile including a lag. As used herein, during a lag an insignificant amount of active agent elutes followed by a period where elution increases as a curve. A lag can include a profile in which elution begins slowly relative to a later accelerated elution rate. Any of a variety of systems can exhibit a lag. For example, a biodegradable top coat can induce a lag.

In an embodiment, the present copolymer compositions provide a desired release profile for the active agent and desirable mechanical properties on the coated article. For example, the present copolymer can provide prolonged release of the hydrophilic, polar, or charged active agent. For example, a stent coated with the present copolymer composition can be expanded and the coating does not crack.

Hemocompatible Compositions

The present invention includes an object including the copolymer on at least a portion of the surface, providing a hemocompatible portion to the surface. The present invention also includes a method of rendering an object hemocompatible, the method including coating at least a portion of the surface of the object with the present copolymer. In certain embodiments, the present composition can be employed in a device, an article, a coating, or a method and can, for example, provide hemocompatibility.

The copolymer can include an effective amount of at least one polar monomeric unit. In an embodiment, the copolymer includes an effective amount of at least one polar monomeric unit and a second monomeric unit. The amount can be effective, for example, to provide a hemocompatible surface as evidenced, for example, by platelet binding below 500 platelets/mm$^2$. In certain embodiments, the hemocompatible surface bound platelets at about 500 platelets/mm$^2$, about 200 platelets/mm$^2$, about 100 platelets/mm$^2$, about 50 platelets/mm$^2$, or about 20 platelets/mm$^2$, about 10 platelets/mm$^2$, or about 5 platelets/mm$^2$. Platelet binding can be determined by known methods. The polar moiety can be in the polymer backbone or a group pendant from the polymer backbone. The second monomeric unit can be polar or non-polar. For example, the second monomeric unit can be hydrophobic in character. In an embodiment, the copolymer is a random copolymer. A random copolymer can include, for example, at least one polar monomeric unit and a second monomeric unit. A random copolymer is not a block copolymer.

Specific embodiments of the copolymer include random copolymers of butyl methacrylate-co-acrylamido-methyl-propane sulfonate (pbma-co-AMPS). In certain embodiments, the random copolymer can include AMPS at about 0.5 to about 30 mol-%, about 5 to about 20 mol-%, about 10 to about 20 mol-%, or about 15 mol-%. The copolymer can include second monomeric unit at about 70 to about 99.5 mol-%, about 80 to about 95 mol-%, about 80 to about 90 mol-%, or about 85 mol-%. The present polymer can include any of these ranges or amounts not modified by about or any of these quantities individually.

Hemocompatibility can be evaluated by any of a variety of known methods. Hemocompatibility can be assessed relative to a control surface, such as a surface of low density polyethylene or a surface of PBMA. Increased hemocompatibility can be determined by demonstrating decreased binding of platelets to a surface or object. The present coated copolymer composition can provide hemocompatibility as evidenced by reduced or insignificant platelet binding to the copolymer composition. Hemocompatibility can be assessed by determining the degree to which platelets bind to an object with the present composition on its exterior compared to the same device with, for example, polybutylmethacrylate (PBMA) or parylene C on its exterior. Platelet binding can be determined by known methods. In certain embodiments, the present coating reduces the number of platelets bound by about 90%, by about 95%, by about 98%, by about 99%, by about 99.9%, or more.

In an embodiment, hemocompatibility can be assessed by determining the degree to which platelets bind to a medical device that has the present composition on its exterior, for example, a stent, when exposed to blood flow, as compared to the same device with, for example, parylene C on its exterior. Platelet binding can be determined by known methods, including, for example, measuring the gamma counts of bound platelets, wherein the platelets have been radiolabeled with, for example, Irvin. In certain embodiments, coating a medical device with the present composition reduces the number of platelets bound when the medical device is exposed to blood flow compared to devices that are not coated, or are coated by conventional compositions known in the art.

In an embodiment, the present copolymer compositions provide a desired level of hemocompatibility and desirable mechanical properties on the coated article. For example, the present copolymer can provide about 99% or more reduction in platelet binding and can provide a coating with acceptable mechanical properties, e.g. coating conformability to the surface of the article or reduced cracking of the coating surface.

Embodiments Including the Present Copolymer Composition

The present invention includes any of a variety of substrates or devices including or coated with the present copolymer composition. In an embodiment, the present invention includes a medical device including a structure configured for introduction into or on a subject and the present copolymer composition disposed on the structure. In an embodiment, the composition includes a pre-polymerized deposited polymer. In an embodiment, the present invention includes a coating including the present copolymer composition. In an embodiment, the present invention includes an article including a core, the core can include the present copolymer composition.

In an embodiment, the present composition can be employed as a blend with another polymer. The other polymer in the blend can be referred to as a second polymer or as a blend polymer. In an embodiment, the blend can include any of a variety of added polymers. The present composition can be employed as a blend with, for example, a hydrophobic polymer such as poly(ethylene-co-vinyl acetate) (PEVA) or poly(n-butyl methacrylate) (PBMA). Suitable polymers for use in blends with the present composition are described hereinbelow.

In an embodiment, the present composition can be employed with another polymer beneath or over the present composition. That is, the present composition can be employed as a component of a layered system of coatings. Suitable polymers for use in layers with the present composition are described hereinbelow.

In an embodiment, the present invention relates to a medical device. The medical device can include a structure configured for treating a subject and a random copolymer composition disposed on the structure. The copolymer composition can include an active agent and a random copolymer. The random copolymer can include a polar monomeric unit. The active agent can be charged, polar, or hydrophobic. In an embodiment, the device can include a random copolymer including butyl methacrylate-co-acrylamido-methyl-propane sulfonate copolymer. The medical device can be configured for introduction into or on a subject.

In an embodiment, the device can include a random copolymer including the acid form of acrylamido-methyl-propane sulfonate. In an embodiment, the device can include a random copolymer including alkali metal salt of acrylamido-methyl-propane sulfonate.

In an embodiment, the device can include or be an implantable device. In an embodiment, the device can include or be configured for use on a surface of a subject (e.g., a wound dressing or tissue sealant). In an embodiment, the device can include a structure including a base material. In an embodiment, the device can include a structure including a surface, the composition being disposed on the surface.

In an embodiment, the active agent can be charged. In an embodiment, the active agent can have a molecular weight of less than 2 kD and has a water solubility of greater than 10 mg/mL at 25° C.

In an embodiment, the device can include a top coat disposed on the random copolymer composition. In an embodiment, the top coat can include a plasma or vapor deposited polymer. In an embodiment, the top coat can include a polymer that does not require a separate initiator (i.e., a self-initiating polymer).

The present invention includes any of a variety of substrates or devices including or coated with the present hemocompatible copolymer composition. In an embodiment, the present invention includes a medical device including a structure configured for introduction into or on a subject and the present hemocompatible copolymer composition disposed on the structure. In an embodiment, the composition includes a pre-polymerized deposited hemocompatible copolymer. In an embodiment, the present invention includes a coating including the present hemocompatible copolymer composition.

In an embodiment, the present hemocompatible copolymer composition can be employed with another polymer beneath the present composition. That is, the present hemocompatible copolymer composition can be employed as a top coat component of a layered system of coatings. Suitable polymers for use in layers with the present composition are described hereinbelow.

In an embodiment, the present invention relates to a medical device. The medical device can include a structure configured for treating a subject and a hemocompatible random copolymer composition disposed on the structure. The hemocompatible random copolymer can include a polar monomeric unit. In an embodiment, the device can include a hemocompatible random copolymer including butyl methacrylate-co-acrylamido-methyl-propane sulfonate copolymer. The medical device can be configured for introduction into or on a subject.

In an embodiment, the device can include a hemocompatible random copolymer including 15 mol-% acrylamido-methyl-propane sulfonate. In an embodiment, the device can include a hemocompatible random copolymer including the acid form of acrylamido-methyl-propane sulfonate. In an embodiment, the device can include a hemocompatible random copolymer including alkali metal salt of acrylamido-methyl-propane sulfonate.

In an embodiment, the device can include or be an implantable device. In an embodiment, the device can include or be configured for use on a surface of a subject (e.g., a wound dressing or tissue sealant). In an embodiment, the device can include a structure including a base material. In an embodiment, the device can include a structure including a surface, the hemocompatible copolymer composition being disposed on the surface.

In an embodiment, the device can include a polymer composition including elutable active agent beneath the hemocompatible random copolymer composition. In such an embodiment, the polymer composition including elutable active agent can include the present random copolymer composition.

Blends and Layers

The present copolymer composition can be employed in any of a variety of configurations with another (e.g. second) polymer. For example, the other polymer can be employed in a blend with the present copolymer. For example, the present composition can be employed as a top coat over or around the other polymer. For example, the other polymer can be beneath or over the present composition in a layered configuration.

A substrate or device including the present copolymer composition can include a blend of the present copolymer composition with a second polymer. A substrate or device including the present composition can also include a top coat of polymer over or around the present composition. A substrate or device including the present composition can include the present composition as a top coat over or around another polymer.

In certain embodiments, the polymer blended or layered with the present copolymer can include at least one polymer. In an embodiment, the layered configuration includes a plurality of polymers, including a first polymer and a second polymer. These first and second polymers can also be employed in blends with the present copolymer composition. When the blend or layered configuration contains only one polymer, it can be either a first or second polymer as described herein. As used herein, term "(meth)acrylate" when used in describing polymers shall mean the form including the methyl group (methacrylate) or the form without the methyl group (acrylate).

Examples of suitable first polymers include poly(alkyl (meth)acrylates), and in particular, those with alkyl chain lengths from 2 to 8 carbons, and with molecular weights from 50 kilodaltons to 900 kilodaltons. An exemplary first polymer is poly(n-butyl methacrylate) (pBMA). Such polymers are available commercially, e.g., from Aldrich, with molecular weights ranging from about 200,000 daltons to about 320,000 daltons, and with varying inherent viscosity, solubility, and form (e.g., as crystals or powder).

Examples of suitable first polymers also include polymers selected from the group consisting of poly(aryl(meth)acrylates), poly(aralkyl(meth)acrylates), and poly(aryloxyalkyl (meth)acrylates). Such terms are used to describe polymeric structures wherein at least one carbon chain and at least one aromatic ring are combined with acrylic groups, typically esters, to provide a composition of this invention. In particular, preferred polymeric structures are those with aryl groups having from 6 to 16 carbon atoms and with weight average molecular weights from about 50 to about 900 kilodaltons. Suitable poly(aralkyl(meth)acrylates), poly(arylalky(meth) acrylates) or poly(aryloxyalkyl(meth)acrylates) can be made from aromatic esters derived from alcohols also containing aromatic moieties. Examples of poly(aryl(meth)acrylates) include poly(9-anthracenyl methacrylate), poly(chlorophenyl acrylate), poly(methacryloxy-2-hydroxybenzophenone), poly(methacryloxybenzotriazole), poly(naphthyl acrylate) and -methacrylate), poly(4-nitrophenyl acrylate), poly(pentachloro(bromo, fluoro)acrylate) and -methacrylate), and poly(phenyl acrylate) and -methacrylate). Examples of poly (aralkyl(meth)acrylates) include poly(benzyl acrylate) and -methacrylate), poly(2-phenethyl acrylate) and -methacrylate, and poly(1-pyrenylmethyl methacrylate). Examples of poly(aryloxyalkyl(meth)acrylates) include poly(phenoxyethyl acrylate) and -methacrylate), and poly(polyethylene glycol phenyl ether acrylates) and -methacrylates with varying polyethylene glycol molecular weights.

Examples of suitable second polymers are available commercially and include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. pEVA co-polymers with lower percent vinyl acetate become increasingly insoluble in typical solvents, whereas those with higher percent vinyl acetate become decreasingly durable.

An exemplary polymer mixture for use in this invention includes mixtures of pBMA and pEVA. This mixture of polymers has proven useful with absolute polymer concentrations (i.e., the total combined concentrations of both polymers in the top coat or blend), of between about 0.25 and about 70 percent (wt). It has furthermore proven effective with individual polymer concentrations in the coating solution of between about 0.05 and about 70 percent (wt). In one preferred embodiment the polymer mixture includes pBMA with a molecular weight of from 100 kilodaltons to 900 kilodaltons and a pEVA copolymer with a vinyl acetate content of from 24 to 36 weight percent. In a particularly preferred embodiment the polymer mixture includes pBMA with a molecular weight of from 200 kilodaltons to 400 kilodaltons and a pEVA copolymer with a vinyl acetate content of from 30 to 34 weight percent.

Second polymers of the invention can also include one or more polymers selected from the group consisting of (i) poly (alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. First polymers of the invention can also include a polymer selected from the group consisting of poly(alkyl (meth)acrylates) and poly(aromatic(meth)acrylates), where "(meth)" will be understood by those skilled in the art to include such molecules in either the acrylic and/or methacrylic form (corresponding to the acrylates and/or methacrylates, respectively).

Poly(alkylene-co-alkyl(meth)acrylates) include those copolymers in which the alkyl groups are either linear or branched, and substituted or unsubstituted with non-interfering groups or atoms. Such alkyl groups preferably include from 1 to 8 carbon atoms, inclusive, and more preferably, from 1 to 4 carbon atoms, inclusive. In an embodiment, the alkyl group is methyl. In some embodiments, copolymers that include such alkyl groups can include from about 15% to about 80% (wt) of alkyl acrylate. When the alkyl group is methyl, the polymer contains from about 20% to about 40% methyl acrylate in some embodiments, and from about 25 to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, second polymers for use in this invention can include ethylene copolymers with other alkylenes, which in turn, can include straight and branched alkylenes, as well as substituted or unsubstituted alkylenes. Examples include copolymers prepared from alkylenes that include from 3 to 8 branched or linear carbon atoms, inclusive. In an embodiment, copolymers prepared from alkylene groups that include from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can include from about 20% to about 90% (based on moles) of ethylene. In an embodiment, copolymers of this type include from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" suitable for use in the present invention includes polymers derived by homopolymerizing or randomly copolymerizing isobutylene, 1-butene and/or 2-butene. The polybutene can be a homopolymer of any of the isomers or it can be a copolymer or a terpolymer of any of the monomeric units in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol or butylated hydroxy toluene (BHT)). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomeric unit with non-aromatic monoolefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl(meth)acrylate and/or isobutylene. In an embodiment, when the mono-olefin monomer is acrylonitrile, the copolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a Mw between about 150 kilodaltons and about 1,000 kilodaltons. In an embodiment, polymers and copolymers have a Mw between about 200 kilodaltons and about 200 kilodaltons with and without BHT.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl(meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have an Mw from about 100 kilodaltons to about 300 kilodaltons.

Polymers of the invention also include biodegradable polymers. Suitable biodegradable polymeric materials are selected from: (a) non-peptide polyamino polymers; (b) polyiminocarbonates; (c) amino acid-derived polycarbonates and polyarylates; and (d) poly(alkylene oxide) polymers. The biodegradable polymeric materials can break down to form degradation products that are non-toxic and do not cause a significant adverse reaction from the body.

Examples of suitable biodegradable polymers include poly(L-lactic acid), polycaprolactone, poly(lactide-co-glycolide), poly(hydroxybutyrate), poly(hydroxybutyrate-covalerate), polydioxanone, polyorthoester, polyanhydride, poly(glycolic acid), poly(D,L lactic acid), poly(glycolic acid-co-trimethylene carbonate), poly(phosphate esters), polyphosphoester urethane, poly(amino acids), cyanoacrylates, poly(trimethylene carbonate), polycarbonates, poly(iminocarbonate), polyesters, copoly(ether-esters), polyalkylene oxalates, polyphosphazenes, and copolymers and blends of the above polymers. Suitable biodegradable polymers include biodegradable biomolecules such as fibrin, fibrinogen, cellulose, dextrans, polysaccharides, starch collagen and hyaluronic acid.

The polymers can include or be a poly(ether ester) multiblock copolymer based on poly(ethylene glycol) (PEG) and poly(butylene terephthalate) and can be described by the following general structure:

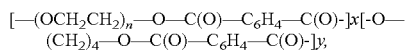

where —$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. Preferably, n is selected such that the molecular weight of the PEG block is between about 300 and about 4000. Preferably, x and y are selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure. In an embodiment, degradation of the copolymer does not create toxic degradation products or an acid environment, and its hydrophilic nature conserves the stability of labile active agents, such as proteins (e.g., lysozymes).

In an embodiment, the biodegradable polymeric material is composed of a non-peptide polyamino acid polymer. Suitable non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

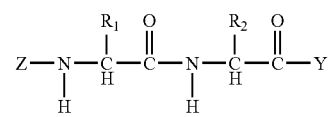

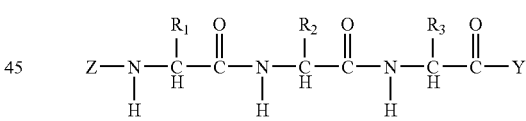

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit includes naturally occurring amino acids that are then polymerized as monomer units via linkages other than by the amide or "peptide" bond. The monomer units can be composed of two or three amino acids united through a peptide bond and thus include dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are biodegradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, alpha aminoadipic acid, canavanine, venkolic acid, thiolhistidine, ergothionine, dihydroxyphenylalanine, and other amino acids well recognized and characterized in protein chemistry.

In an embodiment, the biodegradable polymeric material can be composed of polyiminocarbonates. Polyiminocarbonates are structurally related to polycarbonates, wherein imino groups (>C=NH) are present in the places normally occupied by carbonyl oxygen in the polycarbonates. Thus, the biodegradable component can be formed of polyiminocarbonates having linkages

For example, one useful polyiminocarbonate has the general polymer structural formula

wherein R is an organic divalent group containing a non-fused aromatic organic ring, and n is greater than 1. Preferred embodiments of the R group within the general formula above is exemplified by, but is not limited to the following:

R group

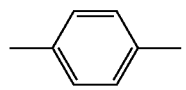 (a)

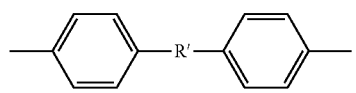 (b)

wherein R' is lower alkene $C_1$ to $C_6$

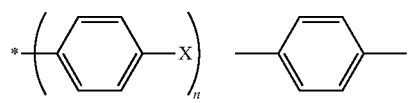 (c)

wherein n is an integer equal to or greater than 1, X is a hetero atom such as —O—, —S—, or a bridging group such as —NH—, —S(=O)—, —SO$_2$—, —C(=O)—, —C(CH$_3$)$_2$—, —CH(CH$_3$)—, —CH(CH$_3$)—CH$_2$—CH(CH$_3$)—,

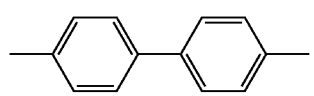 (d)

Also, compounds of the general formula

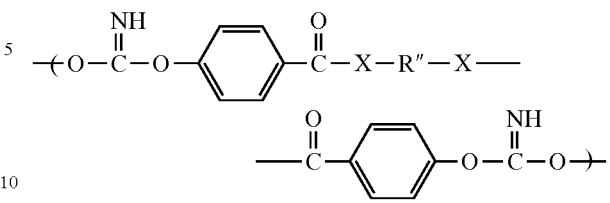

can be utilized, wherein X is O, NH, or NR''', wherein R''' is a lower alkyl radical; and R'' is a divalent residue of a hydrocarbon including polymers such as a polyolefin, an oligoglycol or polyglycol such as polyalkylene glycol ether, a polyester, a polyurea, a polyamine, a polyurethane, or a polyamide. Exemplary starting material for use in accordance with these embodiments include diphenol compounds having the formula

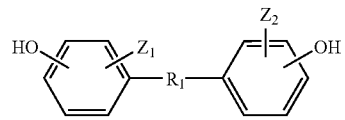

and dicyanate compounds having the formula

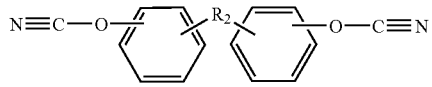

with $R_1$ and $R_2$ being the same or different and being alkylene, arylene, alkylarylene or a functional group containing heteroatoms. $Z_1$, and $Z_2$ can each represent one or more of the same or different radicals selected from the group consisting of hydrogen, halogen, lower-alkyl, carboxyl, amino, nitro, thioether, sulfoxide, and sulfonyl. Preferably, each of $Z_1$ and $Z_2$ are hydrogen.

In an embodiment, the biodegradable polymeric material can be composed of various types of amino acid-derived polycarbonates and polyarylates. These amino acid-derived polycarbonates and polyarylates can be prepared by reacting certain amino acid-derived diphenol starting materials with either phosgene or dicarboxylic acids, respectively. Exemplary amino acid-derived diphenol starting materials for the preparation of the amino acid-derived polycarbonates and/or polyarylates of this embodiment are monomers that are capable of being polymerized to form polyiminocarbonates with glass transition temperatures ("Tg's") sufficiently low to permit thermal processing. The monomers according to this embodiment are diphenol compounds that are amino acid ester derivatives having the formula shown below:

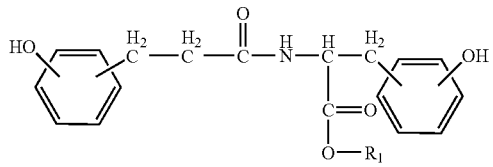

in which $R_1$ is an alkyl group containing up to 18 carbon atoms.

In yet another embodiment, the biodegradable polymeric material can be composed of copolymers containing both hydrophilic poly(alkylene oxides) (PAO) and biodegradable sequences, wherein the hydrocarbon portion of each PAO unit contains from 1 to 4 carbon atoms, or 2 carbon atoms (i.e., the PAO is poly(ethylene oxide)). For example, useful biodegradable polymeric materials can be made of block copolymers containing PAO and amino acids or peptide sequences and contain one or more recurring structural units independently represented by the structure -L-$R_1$-L-$R_2$—, wherein $R_1$ is a poly(alkylene oxide), L is —O— or —NH—, and $R_2$ is an amino acid or peptide sequence containing two carboxylic acid groups and at least one pendent amino group. Other useful biodegradable polymeric materials are composed of polyarylate or polycarbonate random block copolymers that include tyrosine-derived diphenol monomeric units and poly(alkylene oxide), such as the polycarbonate shown below:

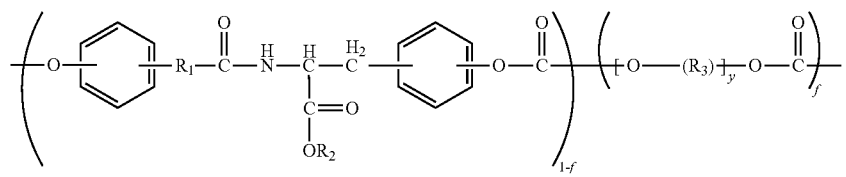

wherein $R_1$ is —CH=CH— or (—$CH_2$—)$_j$, in which j is 0 to 8; $R_2$ is selected from straight and branched alkyl and alkylaryl groups containing up to 18 carbon atoms and optionally containing at least one ether linkage, and derivatives of biologically and pharmaceutically active compounds covalently bonded to the copolymer; each $R_3$ is independently selected from alkylene groups containing 1 to 4 carbon atoms; y is between 5 and about 3000; and f is the percent molar fraction of alkylene oxide in the copolymer and ranges from about 0.01 to about 0.99.

In some embodiments, pendent carboxylic acid groups can be incorporated within the polymer bulk for polycarbonates, polyarylates, and/or poly(alkylene oxide) block copolymers thereof, to further control the rate of polymer backbone degradation and resorption.

The top coat material can also include natural polymers such as polysaccharides such as polydextrans, glycosaminoglycans such as hyaluronic acid, and polypeptides or soluble proteins such as albumin and avidin, and combinations thereof. Combinations of natural and synthetic polymers can also be used. The synthetic and natural polymers and copolymers as described can also be derivatized with a reactive group, for example, a thermally reactive group or a photoreactive group.

Photoactivatable aryl ketones are preferred, such as acetophenone, benzophenone, anthraquinone, quinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

U.S. Pat. No. 5,563,056 (Swan et al.), U.S. Pat. No. 6,214,901 (Chudzik et al.), U.S. published application number 20020041899, now U.S. Pat. No. 7,056,533 (Chudzik et al.), U.S. published application number 20020188037 (Chudzik et al.), and U.S. published application number 20030129130 (Guire et al.), are all herein incorporated by reference.

Active Agents

The copolymer composition of the present invention can also contain one or more active agents, such as biologically active agents. An amount of biologically active agent can be applied to the device to provide a therapeutically effective amount of the agent to a patient receiving the coated device. Particularly useful agents include those that affect cardiovascular function or that can be used to treat cardiovascular-related disorders. In an embodiment, the active agent includes estradiol. In an embodiment, the active agent includes rapamycin.

Active agents useful in the present invention can include many types of therapeutics including thrombin inhibitors, antithrombogenic agents, thrombolytic agents, fibrinolytic agents, anticoagulants, anti-platelet agents, vasospasm inhibitors, calcium channel blockers, steroids, vasodilators, anti-hypertensive agents, antimicrobial agents, antibiotics, antibacterial agents, antiparasite and/or antiprotozoal solutes, antiseptics, antifungals, angiogenic agents, anti-angiogenic agents, inhibitors of surface glycoprotein receptors, antimitotics, microtubule inhibitors, antisecretory agents, actin inhibitors, remodeling inhibitors, antisense nucleotides, antimetabolites, miotic agents, anti-proliferatives, anticancer chemotherapeutic agents, anti-neoplastic agents, antipolymerases, antivirals, anti-AIDS substances, anti-inflammatory steroids or non-steroidal anti-inflammatory agents, analgesics, antipyretics, immunosuppressive agents, immunomodulators, growth hormone antagonists, growth factors, radiotherapeutic agents, peptides, proteins, enzymes, extracellular matrix components, ACE inhibitors, free radical scavengers, chelators, anti-oxidants, photodynamic therapy agents, gene therapy agents, anesthetics, immunotoxins, neurotoxins, opioids, dopamine agonists, hypnotics, antihistamines, tranquilizers, anticonvulsants, muscle relaxants and anti-Parkinson substances, antispasmodics and muscle contractants, anticholinergics, ophthalmic agents, antiglaucoma solutes, prostaglandins, antidepressants, antipsychotic substances, neurotransmitters, anti-emetics, imaging agents, specific targeting agents, and cell response modifiers.

More specifically, in embodiments the active agent can include heparin, covalent heparin, synthetic heparin salts, or another thrombin inhibitor; hirudin, hirulog, argatroban, D-phenylalanyl-L-poly-L-arginyl chloromethyl ketone, or another antithrombogenic agent; urokinase, streptokinase, a tissue plasminogen activator, or another thrombolytic agent; a fibrinolytic agent; a vasospasm inhibitor; a calcium channel blocker, a nitrate, nitric oxide, a nitric oxide promoter, nitric oxide donors, dipyridamole, or another vasodilator; HYTRIN® or other antihypertensive agents; a glycoprotein IIb/IIIa inhibitor (abciximab) or another inhibitor of surface glycoprotein receptors; aspirin, ticlopidine, clopidogrel or another antiplatelet agent; colchicine or another antimitotic, or another microtubule inhibitor; dimethyl sulfoxide (DMSO), a retinoid, or another antisecretory agent; cytochalasin or another actin inhibitor; cell cycle inhibitors; remodeling inhibitors; deoxyribonucleic acid, an antisense nucleotide, or another agent for molecular genetic intervention; methotrexate, or another antimetabolite or antiproliferative agent; tamoxifen citrate, TAXOL®, paclitaxel, or the derivatives thereof, rapamycin (or other rapalogs), vinblastine, vincristine, vinorelbine, etoposide, tenopiside, dactinomycin (actinomycin D), daunorubicin, doxorubicin, idarubicin, anthracyclines, mitoxantrone, bleomycin, plicamycin (mithramycin), mitomycin, mechlorethamine, cyclophosphamide and its analogs, chlorambucil, ethylenimines, methylmelamines, alkyl sulfonates (e.g., busulfan), nitrosoureas (carmustine, etc.), streptozocin, methotrexate (used with many indications), fluorouracil, floxuridine, cytarabine, mercaptopurine, thioguanine, pentostatin, 2-chlorodeoxyadenosine, cisplatin, carboplatin, procarbazine, hydroxyurea, morpholino phosphorodiamidate oligomer or other anti-cancer chemotherapeutic agents; cyclosporin, tacrolimus (FK-506), pimecrolimus, azathioprine, mycophenolate mofetil, mTOR inhibitors, or another immunosuppressive agent; cortisol, cortisone, dexamethasone, dexamethasone sodium phosphate, dexamethasone acetate, dexamethasone derivatives, betamethasone, fludrocortisone, prednisone, prednisolone, 6U-methylprednisolone, triamcinolone (e.g., triamcinolone acetonide), or another steroidal agent; trapidil (a PDGF antagonist), angiopeptin (a growth hormone antagonist), angiogenin, a growth factor (such as vascular endothelial growth factor (VEGF)), or an anti-growth factor antibody (e.g., ranibizumab, which is sold under the tradename LUCENTIS®), or another growth factor antagonist or agonist; dopamine, bromocriptine mesylate, pergolide mesylate, or another dopamine agonist; $^{60}$Co (5.3 year half life), $^{192}$Ir (73.8 days), $^{32}$P (14.3 days), $^{111}$In (68 hours), $^{90}$Y (64 hours), $^{99}$Tc (6 hours), or another radiotherapeutic agent; iodine-containing compounds, barium-containing compounds, gold, tantalum, platinum, tungsten or another heavy metal functioning as a radiopaque agent; a peptide, a protein, an extracellular matrix component, a cellular component or another biologic agent; captopril, enalapril or another angiotensin converting enzyme (ACE) inhibitor; angiotensin receptor blockers; enzyme inhibitors (including growth factor signal transduction kinase inhibitors); ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabeled form or other radiolabeled form of any of the foregoing; an estrogen (such as estradiol, estriol, estrone, and the like) or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluorozinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin, or other antibody targeted therapy agents; gene therapy agents; enalapril and other prodrugs; PROSCAR®, HYTRIN® or other agents for treating benign prostatic hyperplasia (BHP); mitotane, aminoglutethimide, breveldin, acetaminophen, etodalac, tolmetin, ketorolac, ibuprofen and derivatives, mefenamic acid, meclofenamic acid, piroxicam, tenoxicam, phenylbutazone, oxyphenbutazone, nabumetone, auranofin, aurothioglucose, gold sodium thiomalate, a mixture of any of these, or derivatives of any of these.

Other biologically useful compounds that can also be included in the coating material include, but are not limited to, hormones, 0-blockers, anti-anginal agents, cardiac inotropic agents, corticosteroids, analgesics, anti-inflammatory agents, anti-arrhythmic agents, immunosuppressants, anti-bacterial agents, anti-hypertensive agents, anti-malarials, anti-neoplastic agents, anti-protozoal agents, anti-thyroid agents, sedatives, hypnotics and neuroleptics, diuretics, anti-parkinsonian agents, gastro-intestinal agents, anti-viral agents, anti-diabetics, anti-epileptics, anti-fungal agents, histamine H-receptor antagonists, lipid regulating agents, muscle relaxants, nutritional agents such as vitamins and minerals, stimulants, nucleic acids, polypeptides, and vaccines.

Antibiotics are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, geldanamycin, geldanamycin analogs, cephalosporins, or the like. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactan, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Antiviral agents are substances capable of destroying or suppressing the replication of viruses. Examples of anti-viral agents include α-methyl-1-adamantanemethylaamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(−), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacind, 2-cyclooctyl-2-hydroxyethylamine hydrochloride, 2,3-dichloro-α-methylbenzylamine (DCMB), 8,9-dichloro-2,3, 4,5-tetrahydro-1H-2-benzazepine hydrochloride, p-aminoglutethimide, p-aminoglutethimide tartrate R(+), p-aminoglutethimide tartrate S(−), 3-iodotyrosine, alpha-methyltyrosine L(−), alpha-methyltyrosine D(−), cetazolamide, dichlorphenamide, 6-hydroxy-2-benzothiazolesulfonamide, imatinib mesylate (Gleevecg) and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances that have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label that is detectable in vivo, e.g., antibodies attached to fluorescent labels. The term antibody includes whole antibodies or fragments thereof.

Cell response modifiers are chemotactic factors such as platelet-derived growth factor (PDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor alpha, fibroblast growth factor, platelet-derived endothelial cell growth factor, insulin-like growth factor, nerve growth factor, bone growth/ cartilage-inducing factor (alpha and beta), and matrix metalloproteinase inhibitors. Other cell response modifiers are the interleukins, interleukin receptors, interleukin inhibitors, interferons, including alpha, beta, and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins, antisense molecules, androgenic receptor blockers and statin agents.

In an embodiment, the active agent can be in a microparticle. In an embodiment, microparticles can be dispersed in the surface of the copolymer.

The weight of the coating attributable to the active agent can be in any range desired for a given active agent in a given application. In some embodiments, weight of the coating attributable to the active agent is in the range of about 1 microgram to about 10 milligrams of active agent per $cm^2$ of the effective surface area of the device. By "effective" surface area it is meant the surface amenable to being coated with the composition itself. For a flat, nonporous, surface, for instance, this will generally be the macroscopic surface area itself, while for considerably more porous or convoluted (e.g., corrugated, pleated, or fibrous) surfaces the effective surface area can be significantly greater than the corresponding macroscopic surface area. In an embodiment, the weight of the coating attributable to the active agent is between about 0.01 mg and about 0.5 mg of active agent per $cm^2$ of the gross surface area of the device. In an embodiment, the weight of the coating attributable to the active agent is greater than about 0.01 mg.

In some embodiments, more than one active agent can be used in the coating. Specifically, co-agents or co-drugs can be used. A co-agent or co-drug can act differently than the first agent or drug. The co-agent or co-drug can have an elution profile that is different than the first agent or drug.

In some embodiments, the active agent can be hydrophilic. In an embodiment, the active agent can have a molecular weight of less than 1500 daltons and can have a water solubility of greater than 10 mg/mL at 25° C. In some embodiments, the active agent can be hydrophobic. In an embodiment, the active agent can have a water solubility of less than 10 mg/mL at 25° C.

Substrates

Embodiments of the invention provide the ability to deliver active agents from a variety of substrate surfaces including metals, polymers, ceramics, and natural materials.

Metals include, but are not limited to, titanium, stainless steel, and cobalt chromium. Suitable metals can also include the noble metals such as gold, silver, copper, and platinum. Finally, suitable metals can include alloys such as nitinol or cobalt chromium alloys.

Polymers include those formed of synthetic polymers, including oligomers, homopolymers, and copolymers resulting from either addition or condensation polymerizations. Examples include, but not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride, condensation polymers including, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetheretherketone.

Embodiments of the invention can also include the use of ceramics as a substrate. The ceramics include, but are not limited to, silicon nitride, silicon carbide, zirconia, and alumina, as well as glass, silica, and sapphire.

Certain natural materials are also suitable including human tissue, when used as a component of a device, such as bone, cartilage, skin and teeth; and other organic materials such as wood, cellulose, compressed carbon, rubber, silk, wool, and cotton.

The composition of the substrate can also include resins, polysaccharides, silicon, or silica-based materials, glass, films, gels, and membranes.

The substrate can be biodegradable.

Devices

Embodiments of the invention can be used with many different types of devices including medical devices, for example, in which improved hemocompatibility is desirable. Medical devices can include both implantable devices and non-implantable medical devices.

Embodiments of the invention can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraortic balloon pumps, intracardiac suction devices, blood pumps, blood oxygenator devices (including tubing and membranes), blood filters, blood temperature monitors, hemoperfiision units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, tissue sealants, tissue adhesives, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

In some aspects, the polymeric compositions can be utilized in connection with ophthalmic devices. Suitable ophthalmic devices in accordance with these aspects can provide bioactive agent to any desired area of the eye. In some aspects, the devices can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired.

In some aspects, the polymeric compositions can be utilized in connection with ophthalmic devices configured for placement at an external or internal site of the eye. Suitable external devices can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Devices configured for placement at an internal site of the eye can reside within any desired area of the eye. In some aspects, the ophthalmic devices can be configured for placement at an intraocular site, such as the vitreous. Illustrative intraocular devices include, but are not limited to, those described in U.S. Pat. No. 6,719,750 B2 ("Devices for Intraocular Drug Delivery," Varner et al.) and U.S. Pat. No. 5,466,233 ("Tack for Intraocular Drug Delivery and Method for Inserting and Removing Same," Weiner et al.); U.S. Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and 2003/0014036 A1 ("Reservoir Device for Intraocular Drug Delivery," Varner et al.); and U.S. Publication Nos. US2005/0276837 A1 (Controlled Release Bioactive Agent Delivery Device, Anderson et al.), US2005/0271706 A1 (Controlled Release Bioactive Agent Delivery Device, Anderson et al.), US2005/0287188 A1 (Controlled Release Bioactive Agent Delivery Device, Anderson et al.), US2005/0271703 A1 (Controlled Release Bioactive Agent Delivery Device, Anderson et al.), US2005/0281863 A1 (Controlled Release Bioactive Agent Delivery Device, Anderson et al.); and related applications.

In some aspects, the ophthalmic devices can be configured for placement at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. Application No. US2006/0110428 A1 ("Methods and Devices for the Treatment of Ocular Conditions," de Juan et al.); and related applications.

Suitable ophthalmic devices can be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

The present invention may be better understood with reference to the following examples. These examples are intended to be representative of specific embodiments of the invention, and are not intended as limiting the scope of the invention. All numbers that are in percents (%) are percents by weight unless otherwise noted.

EXAMPLES

Example 1

The Present Polymer Compositions Provide Controlled Elution of a Charged Active Agent Butyl methacrylate-co-acrylamido-methyl-propane sulfonate copolymers (pbma-co-AMPS) with the active agent 1,4-di-methyl pyridine iodide (DMPI) incorporated in them provided controlled elution of the active agent.

Experiment 1

Materials and Methods

The poly(n-butyl methacrylate) (pBMA), n-butyl methacrylate (BMA), 2-acrylamido-2-methylpropanesulfonic acid (AMPS), 1,4 dimethylpyridinium iodide (DMPI) were obtained from Aldrich, Milwaukee, Wis. 2,2 Azobis(2,4-dimethylpentanenitrile) (Vazo® 52) was obtained from Dupont, Wilmington, Del. The pBMA was purified by extraction with organic solvent to remove impurities, e.g., residual monomer.

Polymer A: BMA (20 mL, 17.9 g, 126 mmole), AMPS (1.66 g, 8 mmole, 6 mol-%) were dissolved in 60 mL N,N-dimethylformamide (DMF). This reaction mixture, along with a stir bar, was placed into a 120 mL amber jar. The solution was sparged with argon for 45 minutes. The initiator, Vazo® 52 (0.06 g, 0.24 mmole) was added and the jar placed in a 58° C. water bath. The reaction was run for 18 hours and then allowed to cool to room temperature over an additional 2 hours. The reaction mixture was poured into 2000 mL of deionized water at 5° C. to precipitate the polymer. This initial precipitate (1x) was dried 48 hours at 45° C., then placed into vacuum oven at 50° C. for 5 hours. The dried copolymer was dissolved in 50 mL of solvent and this solution was poured into 1800 mL of deionized water at 5° C. to precipitate the polymer. This twice-precipitated copolymer (2x) was collected in a Buchner funnel, rinsed 3 times with 10 mL portions of deionized water at 5° C. The polymer was dried overnight in a fume hood at room temperature, followed by 24 hours in a vacuum oven, also at room temperature.

Polymer B: BMA (18.8 mL, 16.8 g, 118 mmole), AMPS (3.31 g, 16 mmole, 12 mol-%) were dissolved in 60 mL N,N-dimethylformamide (DMF). This reaction mixture, along with a stir bar, was placed in a 120 mL amber jar. The solution was sparged with argon for 45 minutes. The initiator, Vazo® 52 (0.06 g, 0.24 mmole) was added and the jar placed in a 58° C. water bath. The reaction was run for 23 hours and then allowed to cool to room temperature over an additional 2 hours. The reaction mixture was divided in half in order to complete two different precipitation procedures to obtain polymer B and polymer C.

For polymer B, 30 mL (½) of reaction mixture was poured into 1800 mL, deionized water at 5° C. to produce the acid form of the AMPS in the copolymer. The polymer was dried 24 hours at room temperature in a fume hood, followed by 7 hours in a vacuum oven at 40° C. The copolymer was purified by dissolving the polymer into 35 mL of solvent and precipitating into a 1700 mL bath of 5° C. deionized water. The precipitate was collected on a Buchner funnel and rinsed 3 times, with 10 mL, 5° C., deionized water. The copolymer was dried overnight at room temperature, followed by 24 hours in a vacuum oven at room temperature.

Polymer C: The remaining 30 mL of reaction mixture from the polymer B reaction was poured into 1800 mL, 5° C., deionized water containing a stoichiometric amount of NaOH (1 mL, 10 N) to produce the Na$^+$ salt form of AMPS in the co-polymer. The polymer was dried 24 hours at room temperature in a fume hood, followed by 7 hours in a vacuum oven at 40° C. The copolymer was purified by dissolving the polymer into 35 mL of solvent and precipitating into a 1700 mL bath of 5° C. deionized water. The precipitate was collected on a Buchner funnel and rinsed 3 times, with 10 mL, 5° C., deionized water. The copolymer was dried overnight at room temperature, followed by 24 hours in a vacuum oven at room temperature.

Characterization

Analysis of the three poly(n-butylmethacrylate-co-2-acrylamido-2-methylpropansulfonic acid) polymers, A, B and C, on a NMR spectrophotometer, using high-resolution magic angle spin (HRMAS) technique, was consistent with the desired product. $^1$H NMR BL4 HRMAS (CDCl$_3$) AMPS methylene adjacent to sulfate group at 2.8 (broad, 2H) and pBMA, methylene adjacent to ester oxygen at 3.95 (broad, 2H). Integration of the AMPS methylene signal adjacent to sulfate group and pBMA methylene signal adjacent to the ester oxygen indicates that polymer A contains 1.5 mol-% AMPS and polymer B and C contain 3 mol-% AMPS.

Sample Preparation

Coating solutions were prepared in mixed solvent of THF (70%) and methanol (30%) with a DPMI/polymer matrix weight ratio of 15/85 and a solids concentration of 30 mg/mL. This solution was applied to the stents with an ultrasonic coater. The coated stents were dried a minimum of 24 hours under vacuum at ambient temperature prior to in-vitro elution testing.

Elution

The in vitro elution testing was done by suspending the stents in 4 mL of phosphate buffered saline (PBS), pH 7.4, at 37° C. At selected time points the PBS sample media was exchanged with fresh solution and the sample was quantitatively analyzed for content of DPMI or other active agent using a UV/Visible spectrophotometer.

Results

Table 1 shows the various polymers containing DMPI that were coated on stents and analyzed for in vitro elution. Control samples were pBMA coatings containing DMPI. All of the sample coatings were 15/85% (wt/wt), DMPI/polymer or copolymer.

TABLE 1

| Polymer and DMPI drug load of coated stents. | |
|---|---|
| Polymer | DMPI load (µg) |
| A | 200 |
| A | 206 |
| B | 208 |
| B | 194 |
| C | 238 |
| C | 191 |
| pBMA | 144 |
| pBMA | 136 |

FIG. 1 shows the DMPI elution profiles for the samples outlined in Table 1. The initial 24-hour release or "burst" is greatest for the DMPI released from pBMA and smallest from Polymers A and B. Long term sustained release of DPMI was achieved for all formulations.

Experiment 2

Materials and Methods

Polymer D: BMA (17.6 mL, 15.6 g, 110 mmole), AMPS (5.0 g, 24 mmole, 18 mol-%) were dissolved in 60 mL N,N-dimethylformamide (DMF). This reaction mixture, along with a stir bar, was placed in a 120 mL amber jar. The solution was sparged with argon for 1 hour. The initiator, Vazo® 52 (0.06 g, 0.24 mmole) was added and the jar placed in a 58° C. water bath. The reaction was run for 17 hours and then allowed to cool to room temperature over an additional 2 hours. The reaction mixture was divided in half in order to complete two different precipitation procedures to obtain polymer D and polymer E.

For polymer D, 40 mL (½) of reaction mixture was poured into 1800 mL, deionized water at 5° C. to produce the acid form of the AMPS in the copolymer. The polymer was dried 24 hours at room temperature in a fume hood, followed by 24 hours in a vacuum oven at room temperature. The copolymer was purified by dissolving it in 25 mL of solvent and precipitating into a 1500 mL bath of 5° C., deionized water. The precipitate was collected on a Buchner funnel and rinsed 3 times, with 10 mL, 5° C., deionized water. The copolymer was dried overnight at room temperature, followed by 24 hours in a vacuum oven at room temperature.

Polymer E: The remaining 40 mL of reaction mixture from the polymer D reaction was poured into 1800 mL, 5° C., deionized water containing a 5 times stoichiometric excess of NaOH (1 mL, 10 N) to produce the Na$^+$ salt form of AMPS in the copolymer. The polymer was dried 24 hr at room temperature in a fume hood, followed by 24 hours in a vacuum oven at room temperature. The copolymer was purified by dissolving it into 25 mL of solvent and precipitating into a 1500 mL bath of 5° C. deionized water. The precipitate was collected on a Buchner funnel and rinsed 3 times with 10 mL, 5° C., deionized water. The copolymer was dried overnight at room temperature, followed by 24 hours in a vacuum oven at room temperature Characterization Analysis of the two poly(n-butylmethacrylate-co-2-acrylamido-2-methylpropansulfonic acid) polymers, D and E, using $^1$H NMR spectroscopy was consistent with the desired product. $^1$H NMR (THF-d$_8$) AMPS, methylene adjacent to sulfate group 2.8 (broad, 2H) and pBMA, methylene adjacent to ester oxygen 3.95 (broad, 2H). Integration of the AMPS methylene signal adjacent to sulfate group and pBMA methylene signal adjacent to the ester oxygen indicates that polymer D and E contain 9 mol-% AMPS.

Sample Preparation

Two coating solutions were prepared with a DMPI/polymer weight ratio of 15/85 at a solids concentration of 30 mg/mL. Solution 1 was a 70:30, THF:MeOH blend and solution 2 was an 80:20, THF:MeOH blend. These solutions were applied to the stents with an ultrasonic coater. The coated stents were dried a minimum of 24 hours under vacuum at ambient temperature prior to in-vitro elution testing.

Elution

The in vitro elution testing was done as in Experiment 1.

Results

Figure 2:
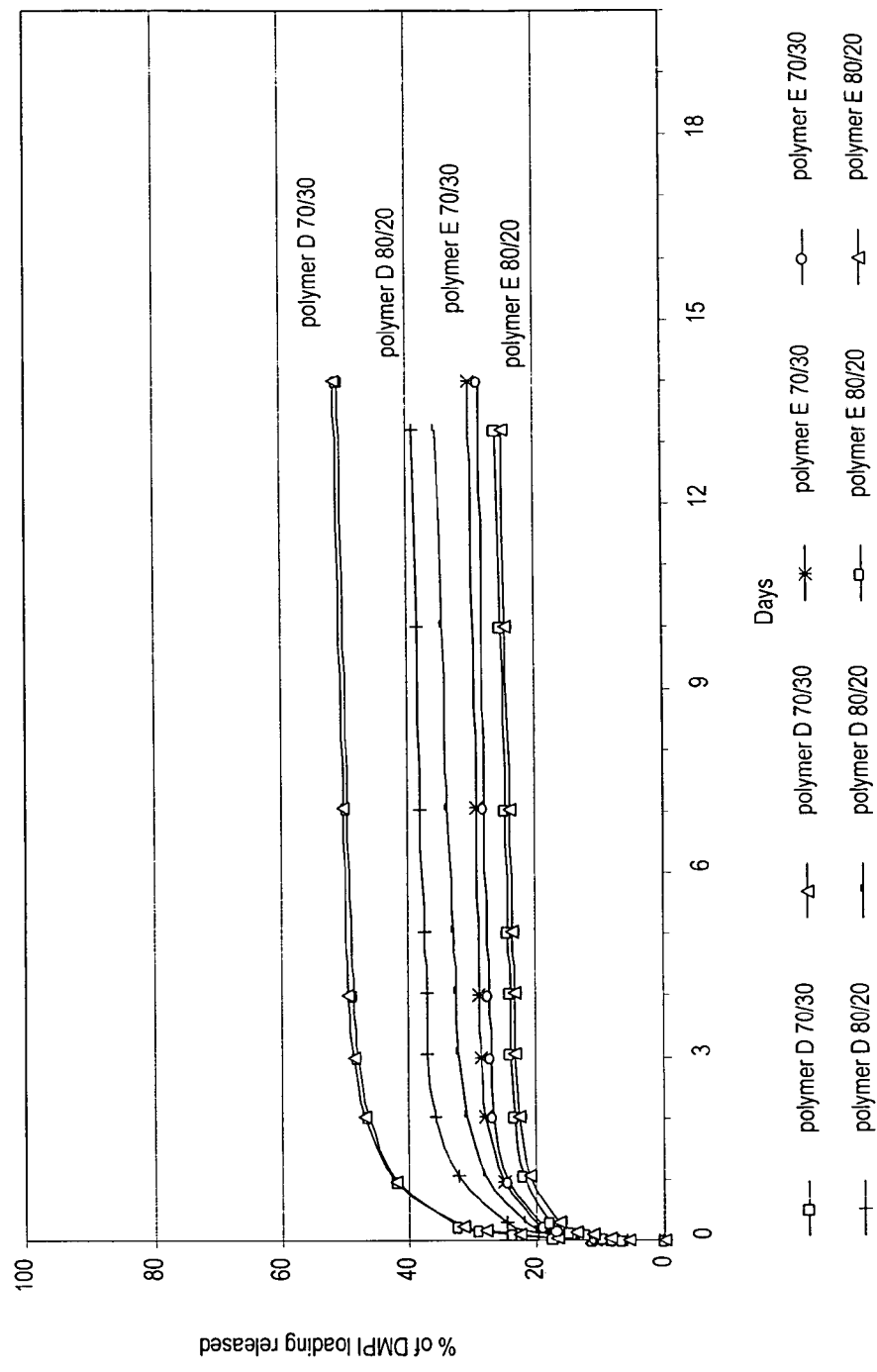
FIG. 2 schematically illustrates the amount of active agent DMPI eluted over time from copolymer coatings according to the present invention.

FIG. 2 contains elution profiles for the active agent DMPI being released from polymer matrices D and E. The elution profiles show the effect of coating solution solvent on drug release. For the two different polymers, the greater the amount of THF relative to methanol in the coating solution the lower the amount of drug released.

Experiment 3

Materials and Methods

The poly(n-butyl methacrylate) (pBMA), n-butyl methacrylate (BMA), 2-acrylamido-2-methylpropanesulfonic acid (AMPS), and 1,4 dimethylpyridinium iodide (DPMI) were obtained from Aldrich, Milwaukee, Wis. 2,2 Azobis(2,4-dimethylpentanenitrile) (Vazo® 52) was obtained from Dupont, Wilmington, Del. The Dialysis tubing (3 Spectra/Por® Membrane MWCO 3,500) was obtained from Spectrum Laboratories, Inc., Rancho Dominguez, Calif.

Polymer B was as prepared and characterized in Experiment 1.

Polymer F: Polymer B (308 mg) was dissolved into THF (4 ml). Dialysis tubing was wetted in a THF/water (50/50) solution. One end of the tubing was tied shut and the polymer solution was poured into the dialysis tubing. The vial that contained the polymer solution was rinsed with THF and the rinse contents were poured into the tubing. The other end of the tubing was tied shut and the tubing was placed into a solution containing THF (560 mL), water (560 mL) and sodium chloride (10 g). The polymer was dialyzed against several of the solutions containing THF, water, and sodium chloride over 3 days to convert the polymer to the sodium salt. The polymer was then dialyzed against deionized water for 3 days to remove the excess sodium chloride. The contents of the dialysis tubing were collected into a round bottom flask, the water was removed by rotary evaporation, and the composition was dried overnight at 55° C. under vacuum in an oven to recover 302 mg of polymer F.

Characterization

Analysis of poly(n-butylmethacrylate-co-2-acrylamido-2-methylpropansulfonic acid), polymer B, was completed in Experiment 1.

Sample Preparation

Coating solutions were prepared in a mixed solvent of THF (80%) and methanol (20%) with a DPMI/polymer matrix weight ratio of 15/85 and a solids concentration of 30 mg/mL. This solution was applied to stents with an ultrasonic coater. The coated stents were dried a minimum of 24 hours under vacuum at ambient temperature prior to in-vitro elution testing.

Elution

The in vitro elution testing was conducted as in Experiment 1.

Results

Figure 3:
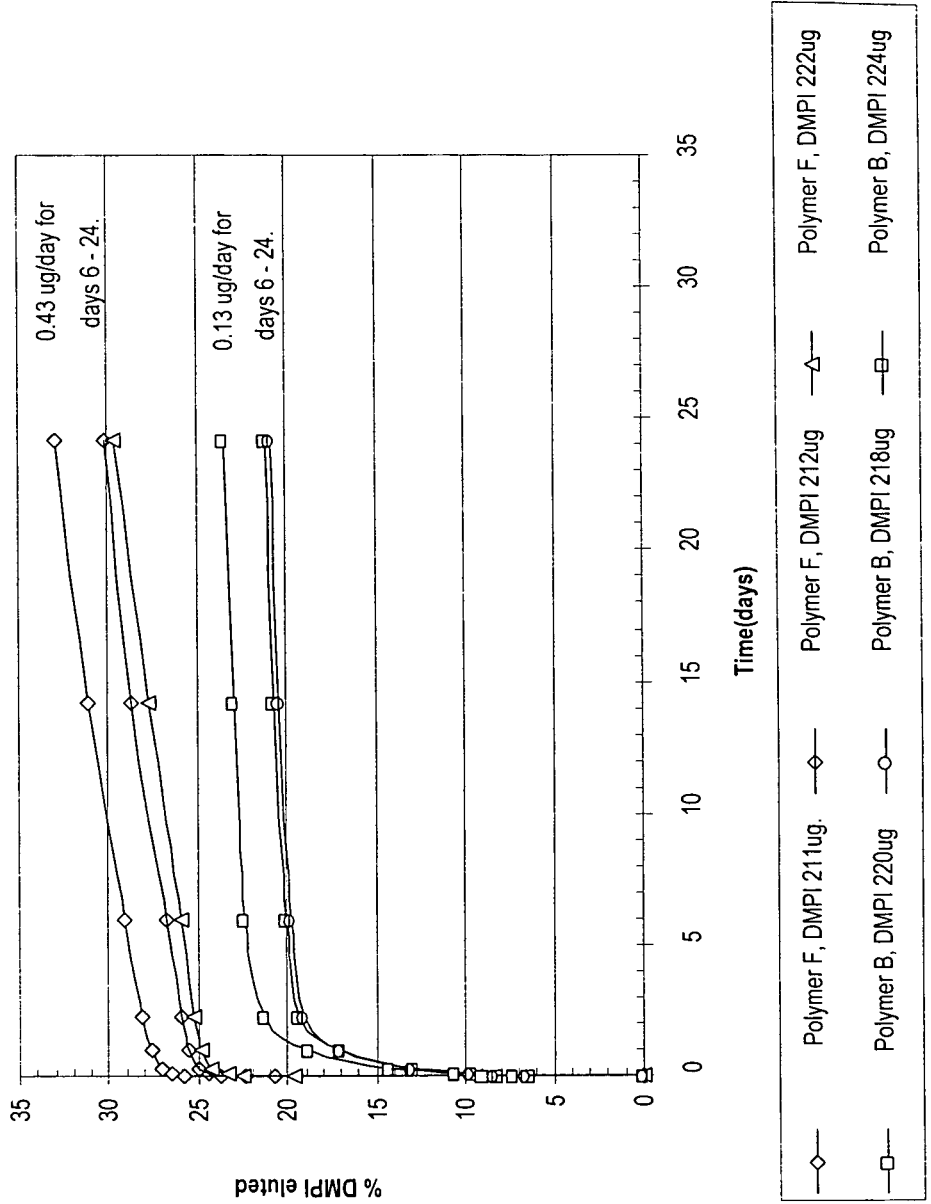
FIG. 3 schematically illustrates the amount of active agent DPMI eluted over time from copolymer coatings according to the present invention.

FIG. 3 shows the DPMI elution profiles for polymer B and polymer F. Polymer F which had been dialyzed to convert it to the sodium salt showed a slightly larger initial one day burst of 26% verses 18% eluted for polymer B. Both polymers showed a linear release of elution from days 6 to 24. Elution of active agent during the linear portion of the graph is 3.3 times faster from polymer F (0.43 µg/day) than from polymer B (0.13 µg/day). Therefore this experiment shows that the acid and salt form of the AMPS can be used to control the drug elution rate.

Example 2

The Present Polymer Compositions Provide Controlled Elution of a Hydrophobic Agent Materials and Methods Triamcinolone acetonide (TA) was obtained from Sigma, St. Louis Mo. Polymers A-D were as in experiments 1 and 2.

Sample Preparation

Coating solutions were prepared in THF as the solvent with a TA/polymer matrix weight ratio of 33/67 and a solids concentration of 30 mg/mL. This solution was applied to the stents with an ultrasonic coater. The coated stents were dried a minimum of 24 hours under vacuum at ambient temperature prior to in-vitro elution testing.

Elution

The in vitro elution testing was done as in Experiment 1.

Results

Table 1 shows the polymers containing TA that were coated on stents and analyzed for in vitro elution. Control samples were PBMA coatings containing TA. All of the sample coatings were 33/67% (wt/wt), TA/polymer or copolymer.

TABLE 2

Polymer and TA drug load of coated stents.

| Polymer | TA load (µg) |
|---------|--------------|
| pBMA | 174 |
| pBMA | 189 |
| A | 217 |
| A | 210 |
| B | 225 |
| B | 225 |
| C | 184 |
| C | 186 |
| D | 188 |
| D | 195 |
| E | 214 |
| E | 219 |

Figure 4:
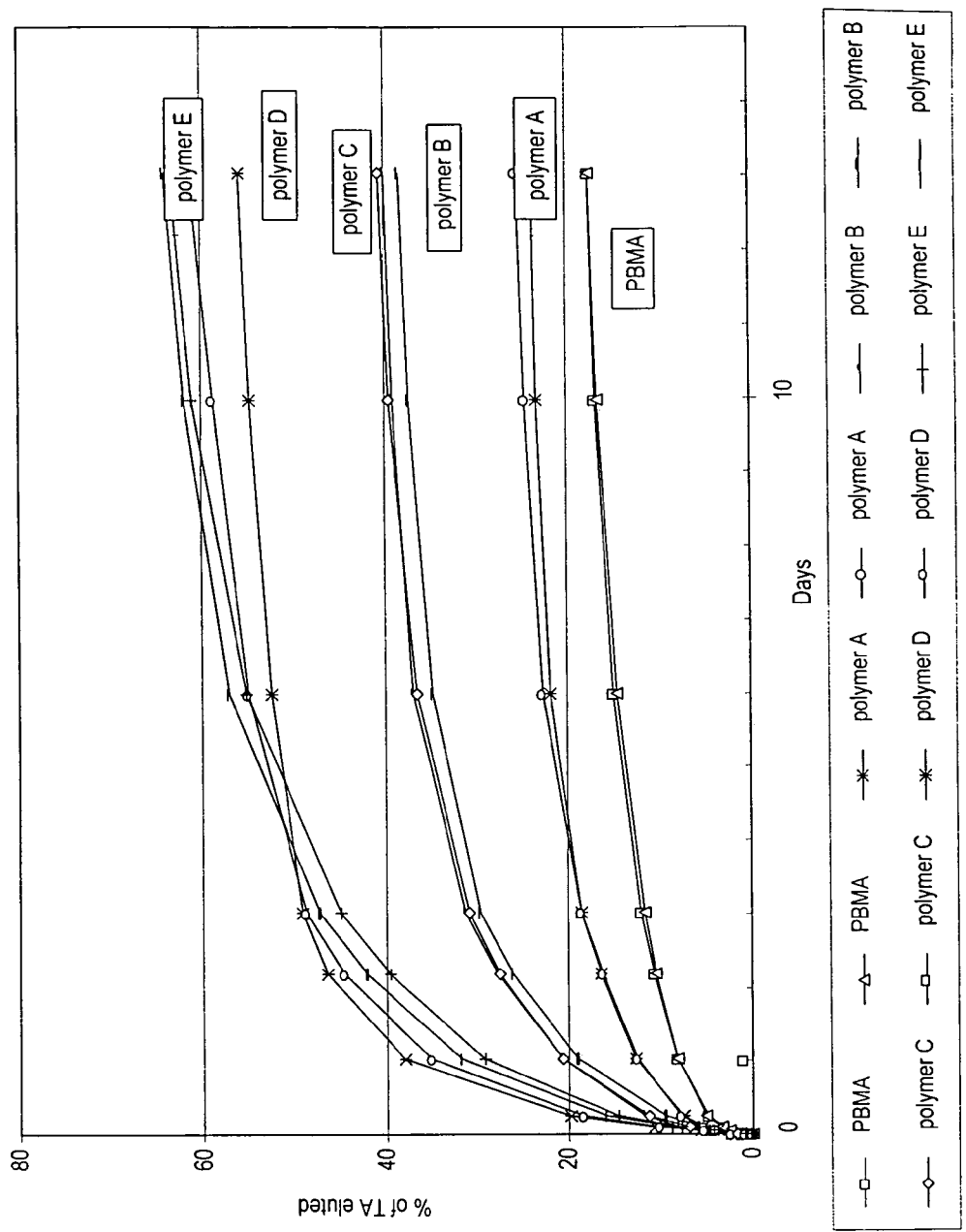
FIG. 4 schematically illustrates the amount of active agent triamcinolone acetonide eluted over time from copolymer coatings according to the present invention.

FIG. 4 shows the TA elution profile, as a percentage of total drug load, for the samples of Table 2. The amount of TA released was controlled by the amount of AMPS that was incorporated into the copolymer. The greatest amount of TA was released from the polymers with the highest amount of AMPS and successively less TA was released as the AMPS concentration in the copolymer was decreased. The least amount of drug was eluted from the PBMA that did not include any AMPS.

Example 3

The Present Polymer Compositions Provide Hemocompatibility

This example determined that a copolymer composition according to the present invention increased hemocompatibility of an object.

Materials and Methods

Platelet rich plasma was prepared by a known method. Blood was collected into coagulation tubes containing 3.8% sodium citrate. The tube was centrifuged at 200 g for 15 minutes at room temperature to obtain a supernatant of platelet rich plasma. Platelet counts in PRP are normally 350,000 to 500,000 platelets/µl.

Photo-pyrrolidone was made as follows: 4-Benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from 1:4 toluene: hexane to give 988 g (91% yield) after drying in a vacuum oven. Product melting point was 92-94° C. Nuclear magnetic resonance (NMR) analysis at 80 MHz (1H NMR (CDCl$_3$)) was consistent with the desired product: aromatic protons 7.20-8.25 (m, 9H). All chemical shift values are in ppm downfield from a tetramethylsilane internal standard. The photo-pyrrolidone was prepared by copolymerization of 1-vinyl-2-pyrrolidone and APMA, followed by photoderivatization of the polymer using 4-benzoylbenzoyl chloride under Schotten-Baumann conditions.

Polymer G: BMA (14.9 mL, 13.3 g, 93.8 mmole), AMPS (8.32 g, 40.2 mmole, 30 mol-%) were dissolved in 60 mL N,N-dimethylformamide (DMF). This reaction mixture, along with a stir bar, was placed in a 120 mL amber jar. The solution was sparged with argon for 1.5 hour. The initiator, Vazo® 52 (0.06 g, 0.24 mmole) was added and the jar placed in a 58° C. water bath. The reaction was run for 19 hours and then allowed to cool to room temperature over an additional 2 hours. The reaction mixture was divided in half in order to complete two different precipitation procedures to obtain polymer G and polymer H.

For polymer G, 40 mL (½) of reaction mixture was poured into 1800 mL, deionized water at 5° C. to produce the acid form of the AMPS in the copolymer. The polymer was dried 24 hours at room temperature in a fume hood, followed by 24 hours in a vacuum oven at room temperature. The copolymer was purified by dissolving it in 25 mL of THF and 15 ml of methanol; placed in dialysis tubing (Spectra/Por membrane, MW cut off of 3500); and in water for 48 hours. The copolymer was dried overnight at room temperature. Polymer H: The remaining 40 mL of reaction mixture from the polymer G reaction was poured into 1800 mL, 5° C., deionized water containing NaOH (3 mL, 10 N) to produce the Na$^+$ salt form of AMPS in the copolymer. The polymer was dried 24 hr at room temperature in a fume hood, followed by 24 hours in a vacuum oven at room temperature. The Na+ form was harder and more brittle than the acid form of the copolymer. The copolymer was purified by dissolving it in 25 mL of THF and 15 ml of methanol; placed in dialysis tubing (Spectra/Por membrane, MW cut off of 3500); and in water for 48 hours. The copolymer was dried overnight at room temperature. Elemental analysis of sulfur content indicated that the polymer G product used for top coating contained approximately 14% AMPS.

Pieces (e.g., 1.5 cm×1.5 cm sheet) of low density polyethylene (LDPE) were coated with:

Photo-pyrrolidone and PBMA over a parylene basecoat;
PBMA-co-(9%)AMPS sodium salt (polymer E) over a parylene basecoat;
PBMA-co-(14%)AMPS acid form (polymer G); or
PBMA-co-(14%)AMPS sodium salt (polymer H) over a parylene basecoat. These samples were exposed to platelet rich plasma for 1 hour at room temperature and washed twice with Tyrode's buffer. The platelets were fixed with formaldehyde in PBS at room temperature. The samples were rinsed with deionized water. The cell membranes were permeabilized with Triton X-100 in phosphate buffered saline (PBS) followed by a PBS rinse.

Platelet adhesion was determined by fluorescent visualization of platelet actin. Briefly: The platelets were visualized with phalloidin-Alexa Fluor 546 (Molecular Probes, A-22283) by incubating in the dark, washing, and viewing them on a slide with the fluorescent microscope. Images shown are 200× images.

Results

Figure 5:
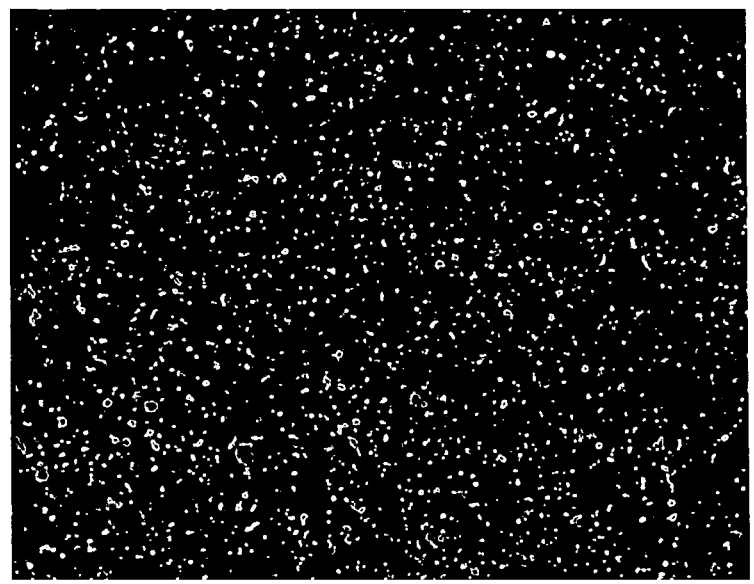
FIG. 5 illustrates a fluorescence micrograph showing platelets bound to a PBMA coated surface.
Figure 6:
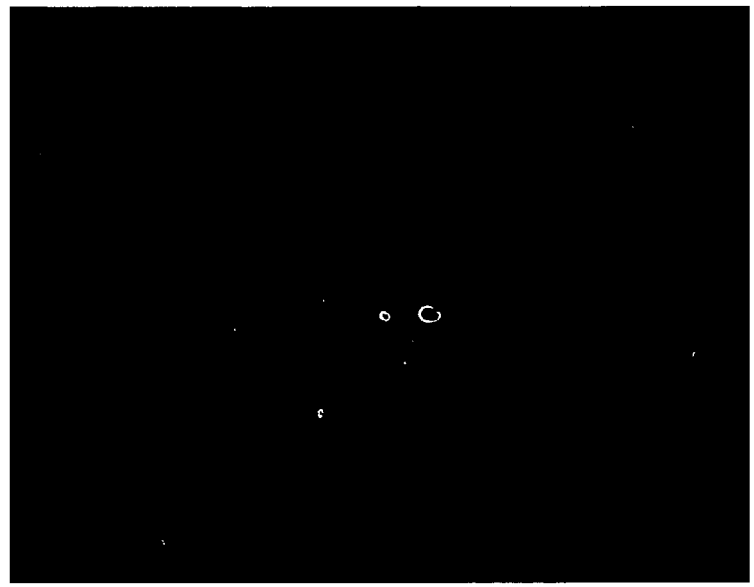
FIG. 6 illustrates a fluorescence micrograph showing a significant reduction in platelets bound to surface coated with PBMA-co(14%)AMPS sodium salt.
Figure 7:
FIG. 7 illustrates a fluorescence micrograph showing a significant reduction in platelets bound to surface coated with PBMA-co(14%)AMPS acid form.

PBMAcoAMPS reduced static human platelet adhesion compared to PBMA (FIGS. 5-7). The samples coated with PBMA-co(14%)AMPS (polymers G and H) surfaces had very few bound platelets (FIGS. 6 and 7), especially the acid form (FIG. 7, polymer G). These images show a highly significant reduction in platelet binding. Copolymer made with 18 mol-% AMPS (polymer E) did not significantly reduce platelet attachment compared to the PBMA coated surface. Uncoated LDPE and photo-pyrrolidone-coated LDPE served as controls and results were as anticipated, i.e., high platelet attachment on uncoated LDPE and low platelet attachment on photo-pyrrolidone coated LDPE.

The samples coated with PBMA-co(14%)AMPS (acid or sodium salt or form, polymers G and H, respectively) appeared more hydrophilic than the PBMA or PBMA-co (9%)AMPS (polymer E) surfaces.

Example 4

Stents Coated With PBMA/AMPS Polymer Compositions Are Hemocompatible in an in vitro Coronary Stent Thrombosis Model This example determined that a PBMS/AMPS copolymer composition coating according to the present invention increased the hemocompatibility of stents in an in vitro coronary stent thrombosis model.

Materials and Methods

Sample Preparation

Heparinized bovine blood was prepared by a known method. Platelets were isolated from the blood and radiolabeled with $^{111}$In using known methods, and then added back to the blood.

Four different coating compositions were applied to stents using an ultrasonic coater. All stents were treated to form a parylene C basecoat (Parylene; Comparative 4A). The remaining stents were further treated to form topcoats using coating solutions containing a therapeutic amount of paclitaxel; a blend of 50% PBMA, 30% PEVA (33% vinyl acetate content), and 20% paclitaxel (PBMA/PEVA/PCLTXL; Comparative 4B) and additionally either a blend of 50% PBMA, 30% PEVA (33% vinyl acetate content), and 20% paclitaxel in a first coating solution, followed by a second coating solution containing 2% PBMA and 98% photo-activatable heparin made as described in U.S. Publication No. 2005/0244453 A1, herein incorporated by reference, (Stucke et al.) (HEP; Comparative 4C) or PBMA-co-(14%)AMPS (Polymer G as described in Example 3) (4D). Table 3 shows the order of the coating compositions applied to the stents tested in the coronary thrombosis model.

TABLE 3

Coating layers on stents for Cornonary Stent Thrombosis Testing.

| Coating Compositions | Base Coat | First Coating | Second Coating |
|---|---|---|---|
| Comparative 4A | Parylene | | |
| Comparative 4B | Parylene | PBMA/PEVA/PCLTXL | |
| Comparative 4C | Parylene | PBMA/PEVA/PCLTXL | HEP |
| 4D | Parylene | PBMA/PEVA/PCLTXL | Polymer G |

The stents were exposed to the heparinized bovine blood for 1 hour using a blood flow loop circuit system, at a temperature of 37° Celsius and a flow rate of approximately 75 ml/min. The parylene C basecoat and PBMA/PEVA/paclitaxel coated stents served as controls.

After termination of the experiment at 1 hour, the stents were removed from the in vitro blood loop system and placed into vials to determine the amount of platelet adhesion, as measured by gamma counting of the labeled platelets Sukavaneshvar et al., *ASAIO J.*, 44, M393-396, 1998).

Results

Results are shown in Table 4.

TABLE 4

$^{111}$In Gamma Counts of Stents After In Vitro Blood Loop Experiment.

| Topcoating Treatment | # of Gamma counts |
|---|---|
| Comparative 4A | 89 ± 15 |
| Comparative 4B | 87 ± 44 |
| Comparative 4C | 62 ± 20 |
| 4D | 65 ± 21 |

The gamma counts of stents having a Polymer G coating over the Parylene® basecoat were noticeably lower than the control stents having a Parylene® or PBMA/PEVA topcoat. The gamma counts of stents with the Parylene® and Polymer G coatings were similar to those of the stents with the heparin second coat. These results suggest that Polymer G surfaces have reduced platelet attachment and anti-thrombogenic properties similar to those of heparinized surfaces when exposed to short-term blood contact.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. An implantable medical device comprising:
   a random copolymer composition disposed on a structure;
   the random copolymer composition and the structure being configured for implanting into a subject;
   the random copolymer composition comprising a therapeutic agent and a butyl methacrylate-co-acrylamidomethyl-propane sulfonate random copolymer; wherein the random copolymer composition provides controlled release of the therapeutic active agent from the medical device into the subject; and wherein the medical device is selected from the group consisting of vascular devices, peripheral cardiovascular devices, surgical devices, orthopedic devices, dental devices, drug delivery devices, ophthalmic devices, urological devices, synthetic prostheses, respiratory devices, neurological devices, ear nose and throat devices, biosensor devices, oncological implants and pain management implants.

2. The device of claim 1, wherein the random copolymer comprises acrylamido-methyl-propane sulfonate at about 1.5 mol-%, about 3 mol-%, or about 9 mol-%.

3. The device of claim 1, wherein the random copolymer comprises acid form of acrylamido-methyl-propane sulfonate.

4. The device of claim 1, wherein the random copolymer comprises alkali metal salt of acrylamido-methyl-propane sulfonate.

5. The device of claim 1, the structure comprising a base material.

6. The device of claim 1, the structure comprising a surface, the composition being disposed on the surface.

7. The device of claim 1, wherein the therapeutic active-agent is charged.

8. The device of claim 1, wherein the therapeutic agent has a molecular weight of less than 2 kD and has a water solubility of greater than 10 mg/mL at 25° C.

9. The device of claim 1, wherein the random copolymer composition comprises a plurality of therapeutic agents.

10. The device of claim 9, wherein the plurality of therapeutic agents comprises a charged therapeutic agent and a hydrophobic therapeutic agent.

11. The device of claim 1, wherein the random copolymer composition further comprises a second (blend) polymer.

12. The device of claim 1, wherein the random copolymer composition is hemocompatible.

13. An implantable medical device comprising:
a random copolymer composition disposed on a structure the random copolymer and the structure being configured for implanting into a subject;
the random copolymer composition comprising a butyl methacrylate-co-acrylamido-methyl-propane sulfonate random copolymer;
wherein the random copolymer composition is hemocompatible; and wherein the medical device is selected from the group consisting of vascular devices, peripheral cardiovascular devices, surgical devices, orthopedic devices, dental devices, drug delivery devices, ophthalmic devices, urological devices, synthetic prostheses, respiratory devices, neurological devices, ear nose and throat devices, biosensor devices, oncological implants, and pain management implants.

14. The device of claim 13, wherein the random copolymer comprises about 10 to about 20 mol-% acrylamido-methyl-propane sulfonate.

15. The device of claim 13, wherein the random copolymer comprises the acid form of acrylamido-methyl-propane sulfonate.

16. The device of claim 13, wherein the random copolymer comprises alkali metal salt of acrylamido-methyl-propane sulfonate.

17. The device of claim 13, further comprising a polymer composition including elutable active agent disposed between the structure and the hemocompatible random copolymer composition.

18. The device of claim 17, wherein the polymer composition including elutable active agent comprises the random copolymer composition.

19. The device of claim 13, the structure comprising a base material.

20. The device of claim 13, the structure comprising a surface, the composition being disposed on the surface.

21. The device of claim 13, wherein the device is implanted into a subject.

22. The device of claim 13, wherein the random copolymer composition further comprises a second (blend) polymer.

23. The device of claim 13, wherein the random copolymer comprises about 15 mol-% acrylamido-methyl-propane sulfonate.

* * * * *